(12) United States Patent
Breuninger et al.

(10) Patent No.: US 8,017,815 B2
(45) Date of Patent: Sep. 13, 2011

(54) PROCESS FOR THE PREPARATION OF HYDROXYTYROSOL

(75) Inventors: Manfred Breuninger, Bad Saeckingen (DE); Marcel Joray, Hochwald (CH)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 12/528,554

(22) PCT Filed: Feb. 28, 2008

(86) PCT No.: PCT/EP2008/001569
§ 371 (c)(1),
(2), (4) Date: Nov. 12, 2009

(87) PCT Pub. No.: WO2008/107109
PCT Pub. Date: Sep. 12, 2008

(65) Prior Publication Data
US 2010/0324343 A1 Dec. 23, 2010

(30) Foreign Application Priority Data

Mar. 7, 2007 (EP) .................................. 07004645

(51) Int. Cl.
*C07C 39/10* (2006.01)
*C07C 39/11* (2006.01)

(52) U.S. Cl. ....................................... 568/764; 568/765
(58) Field of Classification Search .................. 568/764
See application file for complete search history.

(56) References Cited

OTHER PUBLICATIONS

International Search Report for PCT/EP2008/001569, mailed Jun. 27, 2008.
Written Opinion of the International Searching Authority for PCT/EP2008/1569, mailed Jun. 27, 2008.
Baraldi, P.G. et al., "Preparation of 3,4-Dihydroxy-1-benzeneethanol: A Reinvestigation", Liebigs Annalen Der Chemie, (1983), pp. 684-686.
Hidenori, T. et al., "Synthesis of dihydroxyphenacyl glycosides for biological and medicinal study: beta-oxoacteoside from Paulownia tomentosa", Journal of Wood Science, vol. 51, (2005), pp. 48-59.
Voswinckel, H., "Über Derivate des Brenzcatechins", Berichte Der Deutschen Chemischen Gesellschaft, vol. 42, (1910), pp. 4651-4654.

*Primary Examiner* — Sikarl Witherspoon
(74) *Attorney, Agent, or Firm* — Nixon & Vanderhye P.C.

(57) ABSTRACT

Process for the preparation of hydroxytyrosol, characterized by reacting 4-chloroacetyl-catechol with a metal formate and formic acid in an aqueous solvent optionally containing a lower alkanol and catalytically hydrogenating the 4-hydroxy-acetyl-catechol obtained in the presence of a precious metal, preferably on a carrier.

11 Claims, No Drawings

PROCESS FOR THE PREPARATION OF HYDROXYTYROSOL

This application is the U.S. national phase of International Application No. PCT/EP2008/001569 filed 28 Feb. 2008, which designated the U.S. and claims priority to EP Application No. 07004645.3 filed 7 Mar. 2007, the entire contents of each of which are hereby incorporated by reference.

2-(3,4-Dihydroxyphenyl)-ethanol (hydroxytyrosol) is the major member of the group of phenolic compounds present in olive oil in an amount of about 4.2 mg/100 g of extra virgin oil and of about 0.5 mg/100 g of refined oil. The phenolic compounds act synergistically with respect to their antioxidative activities and contribute to a high degree to the valuable nutritive properties of olive oil.

Hydroxytyrosol has attracted a lot of interest during the last years in view of its interesting pharmacological effects. It has a possible favourable role in cardiovascular diseases, could reduce lipidic peroxidation in hepatic microsomes and may have a potent anti-inflammatory effect. These effects make it as well as its pharmacologically acceptable esters valuable ingredients of pharmaceutical and food compositions (EP 1 516 866).

Hydroxytyrosol is so far mainly produced from olive trees, particularly its fruits or its leaves and is on the market as olive liquid or powder extracts, e.g., under the trade mark HIDROX™. It can be prepared synthetically by reduction either of (3,4-dihydroxyphenyl)-acetic acid with, e.g., LiAlH$_4$ (Baraldi, P. G. et al., Liebigs Ann. Chem. 83, 684-686, [1983]), with (trimethylsilyl)-diazomethane and NaBH$_4$ (Bai, C. et al., J. Agric. Food Chem. 46, 3998-4001 [1998]) or with tetrabutylammonium boronate (Tuck, K. L. et al., J. Agric. Food Chem. 48, 4087-4090 [2000]), or of its methyl ester with LiAlH$_4$ (Verhe, R. et al., Bull. de Liaison—Groupe Polyphenols 16(2), 237-244 [1992]) which again can be obtained by esterification of (3,4-dihydroxyphenyl)-acetic acid (see Bai, supra). (3,4-dihydroxyphenyl)-acetic acid can be prepared from 3,4-dihydroxymandelic acid which is obtainable from catechol and glyoxylic acid as described, e.g., by Bjørsvik et al. (Org. Process Res. & Development 49, 537-543 [2000]).

Applicant has now found a new, economically effective, technically attractive approach to hydroxytyrosol starting from 4-chloroacetyl-catechol via 4-hydroxyacetyl-catechol. 4-chloroacetyl-catechol is commercially available or can be made from catechol according to, e.g., Schayer, R. W. (J. Am. Chem. Soc. 74., 2441 [1952]) or Levin, N. and Hartung, W. H. (J. Org. Chem. 7, 408-415 [1942]).

While the catalytic hydrogenation of benzylic oxo groups to methylene groups is wen-known it is interesting to note that although hydroxytyrosol is a compound of high interest so far its preparation from 4-hydroxyacetyl-catechol by catalytic hydrogenation has not been described and not been considered so far.

Preparation of 4-hydroxyacetyl-catechol from 4-chloroacetyl-catechol has been described by Tozuka, H. et al. (J. Wood Sci. 51, 48-59 [2005]). However, this reaction is carried out in two steps, via the tri-acetate, within more than 40 hours and with a yield of only 65%. Consequently, 4-chloroacetyl-catechol, does not recommend itself as a starting material for a technically attractive synthesis of hydroxytyrosol. In accordance with the present invention, it has now been found that 4-hydroxyacetyl-catechol can be obtained in a yield of about 95% within a shorter period of time from 4-chloroacetyl-catechol in a one step reaction, by reacting the latter with a metal formate and formic acid in an aqueous solution that may optionally contain a lower alkanol. The possibility of hydrogenation of 4-hydroxyacetyl-catechol in the presence of catalytic amounts of a precious metal catalyst represents an attractive new approach for the chemical synthesis of hydroxytyrosol, compared with the use of stoichiometric amounts plus an excess of expensive complex metal hydrides, such as NaBH$_4$, LiBH$_4$ or LiAlH$_4$ in prior art syntheses.

The present invention, therefore, relates to a process for the preparation of hydroxytyrosol by reacting 4-chloroacetyl-catechol with a metal formate and formic acid in an aqueous solution to 4-hydroyacetyl-catechol followed by catalytic hydrogenation of the obtained 4-hydroxyacetyl-catechol in the presence of a precious metal catalyst on a carrier.

The present invention, however, also relates to the two reaction steps separately, i.e., on the one hand to the process for the preparation of hydroxytyrosol by catalytic hydrogenation of 4-hydroxyacetyl-catechol with a precious metal catalyst on a carrier and on the other hand to the reaction of 4-chloroacetyl-catechol with a metal formate and formic acid in an aqueous solvent to give 4-hydroxyacetyl-catechol.

The cleavage of a benzylic carbon oxygen bond is well known to a person skilled in the art. Such a hydrogenolysis is effected normally with a supported Palladium catalyst, e.g. Pd/C in a polar solvent like water, alcohol or even acetic acid and is said to be promoted by acid (e.g. perchloric acid) as published (P. N. Rylander: Catalytic hydrogenation over Platinum Metals, Academic Press 1967, page 449 ff.; or "The catalyst technical handbook" © 2005 Johnson Matthey Plc, page 29; or Ph. M. Manoury et al., J. Med. Chem. 1987, 30, 1003-1011).

Compared with the published procedures the present hydrogenation comprises several differences:

(1) In water and other polar solvents like alcohol the hydrogenolysis does not take place. It has now been found that non protic solvents of low polarity are most suitable, e.g., t-butyl methyl ether (TBME) or ethyl acetate. But strictly anhydrous conditions are also not ideal. Best results are found when a small amount (e.g. about 1 mol) of water is present.

(2) In the presence of strong acids, e.g., HClO$_4$, H$_2$SO$_4$ or HCl, high amounts of side products are formed. Best results were obtained under strictly acid free conditions. But the presence of free base, e.g., NaOH or sodium bicarbonate, retards or even prevents the reaction.

(3) Hydrogenolysis of the carbonyl oxygen is also possible with a ruthenium catalyst.

The hydrogenation of 4-hydroxyacetyl-catechol can be carried out in the presence of a moist solvent in a manner known per se and is preferably carried out in the presence of a liquid alkyl ester of a carboxylic acid, e.g., ethyl acetate, or an ether, e.g., a di-C$_{1-5}$-alkyl ether or cyclic 5- to 6-ring ether like THF, most preferably tert.-butyl-methyl or tert.-butyl-ethyl ether, and in the presence of a precious metal catalyst, e.g., Pd or Ru, preferably on a solid carrier, most preferably in the presence of Pd/C or Ru/C, at a temperature from 0 to 60° C., preferably from 30-50° C., preferably after evacuation at a hydrogen pressure of at least higher than the vapor pressure of the solvent at the hydrogenation temperature. It is not important that the starting material is completely dissolved at the beginning of the hydrogenolysis. Complete conversion is also possible when a slurry of 4-hydroxyacetyl-catechol in a solvent is treated with hydrogen in presence of a precious metal catalyst. The pressure is preferably from normal, i.e. atmospheric pressure, to 10 bar or higher.

The transformation of 4-chloroacetyl-catechol into 4-hydroxyacetyl-catechol is easily achieved in high yield by the reaction of 4-chloroacetyl-catechol with a metal formate, preferably an alkali or alkaline earth metal, most preferably sodium formate, and formic acid in an aqueous solution, optionally containing a lower alkanol, i.e., a C$_{1-5}$-alkanol, preferably ethanol. The most preferred solvent, however, is water. The 4-hydroxyacetyl-catechol can be isolated from the reaction mixture by filtration optionally after acidification with hydrochloric acid to a pH of about 1 to 0 and crystallization from the cooled solution. To improve the yield and purity, work up of the mother liquor and recrystallization from water is recommended. An alternative isolation of the product can be achieved by extraction of the cooled (ca. 30° C.) reaction mixture optionally after acidification with hydrochloric acid to a pH of about 0.5. For the extraction a solvent poorly mixable with water, e.g., ethyl acetate, is recommended. Other solvents like dichloromethane or diethyl ether are less preferable for ecological or solubility reasons. After removal of the extraction solvent a crude, sufficiently pure material is obtained. This crude 4-hydroxyacetyl-catechol can be used for the next step without further purification. For the conversion of the 4-chloroacetyl-catechol to the 4-hydroxyacetyl-catechol it is essential to use a reaction mixture of an acid and a metal salt of an acid, preferably a relatively weak acid, preferably a carboxylic acid, most preferably formic acid, which is in aqueous solution. Using only, e.g., sodium formate or potassium carbonate without the weak acid results in mixtures with a lower isolated yield. The salt is required at least in an amount equivalent to the 4-chloroacetyl-catechol but an excess is preferable although not critical. Preferred is an excess of about 50%, on a molar basis. Also the amount of the free acid is not critical as long as the reaction mixture is at least slightly acidic. But even without acid added the hydrolysis occurs, though with reduced selectivity, as mentioned above. So most preferred is an amount of formic acid equivalent to the formate. The pH of the resulting solution is then between about 3.5 and about 4.0.

Other carboxylic acids like acetic, fumaric or malonic acid, which form easy hydrolysable esters can be used instead of formic acid as free acids as well as their corresponding salts. The product, however, then consists of the 4-hydroxyacetyl-catechol and its corresponding 4-acyloxyacetyl-catechol that can be converted to 4-hydroxyacetyl-catechol by known methods.

The mode how the acid and the salt are placed in the solution is not critical. One can add the salt and the acid. But also one can add the acid and neutralize it partially by addition of the needed amount of the appropriate base. And a third mode is to liberate the required (weak) acid from the salt by addition of the required amount of a strong acid like hydrochloric acid or sulfuric acid to a solution of the salt.

The invention is described in more detail in the following Examples.

EXAMPLE 1

Preparation of 4-chloroacetyl-catechol

Similar to the procedures of R. W. Schayer (J. Am. Chem. Soc. 74, 2441 [1952]) and N. Levin et al. (J. Org. Chem. 7, 408-415 [1942]), but without an additional solvent, a mixture of 100 g catechol, 750 g (450 ml) of phosphorus oxychloride and 206 g (145 ml) of chloracetyl chloride was stirred at reflux temperature (ca. 125° C.) in an argon atmosphere for 4.5 hours. Then most of the volatiles were distilled off at 80° C. (bath temperature) and, finally, under reduced pressure. To the nearly intractable dark mass were added at ca 80° C. 200 ml of water upon which the mixture became stirabel again. 600 ml of cold (0° C.) water were added in portions to control the exothermic reaction. When all of the water was added and the exothermic reaction had ceased the mixture was stirred for 2 hours under reflux. Upon stirring over night without further heating 125 g of crude product precipitated as dark brown crystals with a purity of about 90% (yield ca. 65%).

EXAMPLE 2

Preparation of 4-hydroxyacetyl-catechol (Isolation by Crystallization)

A 1 liter reactor equipped with a reflux condenser and magnetic stirring bar was charged under argon with 45 g of 4-chloroacetyl-catechol of a purity of ca. 90%, 260 ml of ethanol, 130 ml of water, 38 g of sodium formate and 17 ml (~21 g) of formic acid. The stirred mixture was heated under reflux (~100° C.) for 24 hours. Under vacuum a part of the solvents was distilled off. The remaining solution of about 100 ml was acidified by addition of 35.5 g of conc. hydrochloric acid (37%) resulting in a pH of about 0.5. 200 ml of water were added and the mixture was refluxed for 10 minutes. Upon stirring over night without heating crystals separated. The slurry was filtered by suction and the crystals were washed with 50 ml of cold water. After drying over night at 70° C. at ~20 mbar the yield of 4-hydroxyacetyl-catechol was 34.2 g with a purity of 89.2% corresponding to a yield of 82.6%. In the mother liquors additional 14% of the product was detected by analysis.

EXAMPLE 3

Preparation of 4-hydroxyacetyl-catechol (Isolation by Extraction)

A 0.1 liter reactor equipped with a reflux condenser and magnetic stirring bar was charged under argon with 5.05 g of 4-chloroacetyl-catechol of a purity of ca. 99%, 50 ml of water, 2.8 g of sodium formate and 1.55 ml (~1.9 g) of formic acid. The stirred mixture was heated under reflux (~100° C.) for 22 hours. The solution was cooled to about 25° C. and acidified by addition of 2 g of conc. hydrochloric acid (37%) resulting in a pH of about 0.5. The mixture was extracted with ethyl acetate, once with 100 ml then 3 times with 50 ml each. The organic extracts have been back washed 3 times with 30 ml 10% brine. The combined organic phases were dried with sodium sulfate, filtered and evaporated at reduced pressure at 40° C. This resulted in a light tan solid crystalline product of 4.56 g of 97.4% purity corresponding to a yield of 98.9%.

EXAMPLE 4

Preparation of 4-hydroxyacetyl-catechol (Isolation by Extraction after Awing More HCl)

A 1 liter reactor equipped with a reflux condenser and magnetic stirring bar was charged under argon with 50.5 g of 4-chloroacetyl-catechol of a purity of ca. 99%, 500 ml of water, 28 g of sodium formate and 15.5 ml (~19 g) of formic acid. The stirred mixture was heated under reflux (~100° C.) for 22 hours. The solution was cooled to about 25° C. and acidified by addition of 36.6 g of conc. hydrochloric acid (37%) resulting in a pH of about 0.5. The mixture was extracted with ethyl acetate, once with 1 l then 3 times with 0.5 l each. The organic extracts have been back washed 3 times with 300 ml 10% brine. The combined organic phases were dried with sodium sulfate, filtered and evaporated at reduced pressure at 40° C. and dried at 45° C. at ~0.5 mbar. This resulted in a light tan solid crystalline product of 44.63 g of 96.4% purity corresponding to a yield of 95.9%. Analyses showed this material to have a contamination of 0.12% sodium ions and 0.03% chloride ions.

EXAMPLE 5

Preparation of Hydroxytyrosol (Influence of Catalyst)

A special house made pressure reactor, a 50 ml 10 bar glass reactor with steel mantle and a magnetic stirring bar, was charged with catalyst, 4-hydroxyacetyl-catechol (produced according to Example 2) and t-butyl methyl ether. The reactor was evacuated and filled with hydrogen. Hydrogenation was started by stirring at 5 bar hydrogen pressure while heating to 40° C. By the end of the reaction the hydrogen was replaced by air, the slurry was filtered, the catalyst was washed with ethyl acetate. After evaporation of the solvents and drying at 1 mbar the product was analyzed quantitatively. The details of some reactions and the results are shown in Table 1.

TABLE 1

| Example | Starting material: amount | Catalyst type | Catalyst amount | Solvent TBME | Product Amount | Analytical purity | Yield |
|---|---|---|---|---|---|---|---|
| 5 | 3 g | 10% Pd/C | 0.3 g | 30 ml | 2.92 g | 68.1% | 75.4% |
| 5 | 1.5 g | 5% Ru/C | 0.15 g | 30 ml | 1.5 g | 72.2% | 82.1% |
| 6 | 30 g | 10% Pd/C | 3 g | 300 ml | 27.7 | 66.6% | 68.6% |

EXAMPLE 6

Preparation of Hydroxytyrosol (Different Reactor)

A 1 l autoclave was used for the hydrogenation as described in Example 5. After replacement of air by hydrogen the mixture was heated to 40° C. under 1 atm hydrogen. Then hydrogen pressure was increased to 10 bar. The details are given in Table 1.

EXAMPLE 7

Preparation of Hydroxytyrosol (Influence of Added Acids)

In a reactor as described in Example 5 samples of 1.5 g of 4-hydroxyacetyl-catechol low in sodium and chloride (<0.1%) were hydrogenated in the presence or absence of added strong acid. All reactions were run with 0.15 g Pd/C (10%) in 30 ml of solvent at 5 bar and 40° C. at least to the end of hydrogen uptake. The catalyst was filtered off and washed with ethyl acetate. The solutions were concentrated and the residues analyzed quantitatively. The results are summarized in Table 2 showing the influence of the acids. The starting material was totally consumed in every experiment with the exception of the one with sulfuric acid (7.3% remained finally).

TABLE 2

Influence of added acids.

| Starting material | | Acid added | | Time | Solvent | Product | | |
|---|---|---|---|---|---|---|---|---|
| amount | mmol | | amount mmol | h | 30 ml | amount g | analytical purity | yield |
| 1.5 g | 8.4 | none | | 7 | TBME | 1.50 | 73.9% | 85.3% |
| 1.5 g | 8.4 | HClO$_4$ | 0.42 | 2.1 | TBME | 1.45 | 29.1% | 32.5% |
| 1.5 g | 8.4 | H$_2$SO$_4$ | 0.42 | 1.5 | TBME | 1.35 | 18.4% | 19.1% |
| 1.5 g | 8.6*) | HCl | 0.12 | 2 | ethyl acetate | 1.48 | 67.7% | 75.9% |

*)higher purity.

EXAMPLE 8

Preparation of Hydroxytyrosol (Influence of Added Water)

In a reactor as described in Example 5 well dried samples of 1.5 g of 4-hydroxyacetyl-catechol with very low sodium and chloride content (<0.15%) were hydrogenated in the presence or absence of added water. All reactions were run with 0.15 g Pd/C (10%) in 30 ml of solvent at 5 bar and 40° C. at least to the end of hydrogen uptake. The catalyst was filtered off and washed with ethyl acetate. The solutions were concentrated and the residues analyzed quantitatively. The results are summarized in Table 3 snowing the influence of the added water. The starting material was totally consumed in every experiment at the end. The data shows that the result is clearly improved at a relation of 1 mol water added per 3 moles of 4-hydroxyacetyl-catechol and is even better at a relation of 1/1 mole. The lower suitability of methanol as solvent is also demonstrated.

TABLE 3

Influence of solvent and of added water.

| Starting material | | Water added | Time | Solvent | Product | | |
|---|---|---|---|---|---|---|---|
| amount | mmol | mmol | h | 30 ml | amount g | analytical purity | yield |
| 1.5 g | 8.6 | none | 7 | TBME | 1.52 | 47.5% | 54.7% |
| 1.5 g | 8.6 | 2.8 | 25 | TBME | 1.19 | 78.0% | 87.0% |
| 1.5 g | 8.6 | 8.9 | 7.5 | TBME | 1.56 | 75.3% | 88.5% |
| 1.5 g | 8.6 | 8.9 | 16 | ethyl acetate | 1.50 | 77.6% | 87.8% |
| 1.5 g | 8.6 | 8.9 | 15 | methanol | 1.42 | 69.9 | 75.2 |

The invention claimed is:

1. A process for the preparation of hydroxytyrosol which comprises reacting 4-chloroacetyl-catechol with a metal formate and formic acid in an aqueous solution and catalytically hydrogenating the 4-hydroxyacetyl-catechol obtained in the presence of a precious metal catalyst.

2. A process for the preparation of hydroxytyrosol which comprises catalytically hydrogenating 4-hydroxyacetyl-catechol in the presence of a precious metal catalyst.

3. A process for the preparation of 4-hydroxyaretyl-catechol which comprises reacting 4-chloroacetyl-catechol with a metal formate and formic acid in an aqueous solution.

4. A process as claimed in claim 1 or 2, wherein the precious metal is palladium or ruthenium.

5. A process as claimed in claim 4, wherein the hydrogenation is carried out in a di-$C_{i5}$-alkyl-ether.

6. A process as claimed in claim 4, wherein the hydrogenation is carried out in a liquid alkyl-ester.

7. A process as claimed in claim 1, wherein the aqueous solution comprises a lower alkanol or water as a solvent.

8. The process according to claim 1 or 2, wherein the precious metal catalyst is on a solid carrier.

9. A process as claimed in claim 8, wherein the precious metal catalyst on a carrier is Pd/C or Ru/C.

10. A process as claimed in claim 5, wherein the hydrogenation is carried out in tertiary-butyl-methyl ether or tertiary-butyl-ethyl ether.

11. A process as claimed in claim 6, wherein the liquid alkyl-ester is ethyl acetate.

\* \* \* \* \*